United States Patent [19]

Keefe et al.

[11] Patent Number: 5,230,426

[45] Date of Patent: Jul. 27, 1993

[54] HYPODERMIC NEEDLE DISPOSAL SYSTEM

[76] Inventors: Daniel Keefe; Susan Burns, both of 230 Willow Ridge Dr., Amherst, N.Y. 14228

[21] Appl. No.: 944,335

[22] Filed: Sep. 14, 1992

[51] Int. Cl.⁵ .................. B65D 81/18; B65D 85/24
[52] U.S. Cl. ................... 206/205; 206/366; 220/507
[58] Field of Search ............ 206/363, 365, 366, 370, 206/438, 205; 220/507, 554

[56] References Cited

U.S. PATENT DOCUMENTS

| | | | |
|---|---|---|---|
| 2,557,420 | 6/1957 | Elliot | 206/366 |
| 2,835,377 | 5/1958 | May et al. | 206/366 |
| 4,919,264 | 4/1990 | Shinall | 206/366 |
| 4,946,035 | 8/1990 | Grimm et al. | 206/366 |
| 4,973,315 | 11/1990 | Sincock | 206/365 |
| 5,038,929 | 8/1991 | Kubofcik | 206/365 |
| 5,129,886 | 7/1992 | Sincock | 206/365 |

*Primary Examiner*—Jimmy G. Foster
*Attorney, Agent, or Firm*—Robert J. Bird

[57] ABSTRACT

A hypodermic needle disposal system includes a housing forming an array of parallel cells, each to receive a tube containing a bonding resin. Each tube includes a rupture seal on its front end. A used needle is directed into a tube to pierce its rupture seal and embed itself in resin. When the resin bonds on the needle, the needle and tube are together removed from the cell for disposal. Tubes are restrained from free movement and from sliding out of their cells by a gravity locking engagement with the housing.

3 Claims, 1 Drawing Sheet

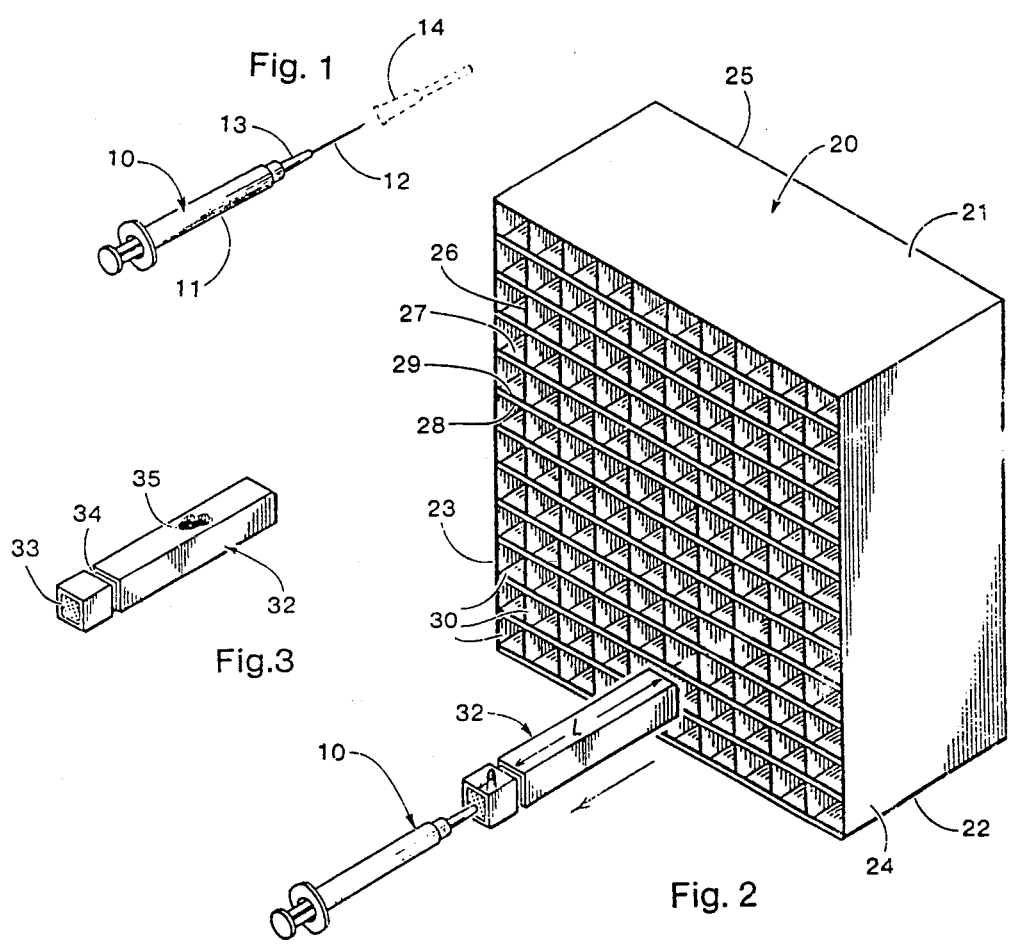

HYPODERMIC NEEDLE DISPOSAL SYSTEM

FIELD OF THE INVENTION

This invention is a safe disposal system for hypodermic needles. The system is a method and means for embedding a needle in a flat bonding resin to form a protective coating.

BACKGROUND INFORMATION

Handling and disposal of hospital refuse and other medical refuse has always been a problem because of the possibility of infection from contact with it. Hypodermic needles and other sharp medical instruments are items of special concern. A needle which is HIV contaminated is a potentially deadly instrument.

A typical hypodermic syringe has a removable protective needle cap which fits over the needle and is held in place by frictional or threaded engagement with the needle hub. The cap is a small slender piece. Once it is removed, replacing it over the needle is risky. Such practice is discouraged. Used syringes are sometimes simply dropped on the floor during life saving treatment in a trauma center or emergency room, creating a danger to anyone involved in the emergency and to those cleaning up or walking on the debris. These risks exist even in normal use of these devices, until they are properly disposed of.

Needle sticks account for 35% of the hospital-related injuries. There were 800,000 needle stick injuries reported in 1987. These statistics clearly show a needle for improved apparatus and techniques for handling needles.

It is an object of this invention to provide a hypodermic needle disposal system which is effective and which will encourage use because of its simplicity and convenience.

U.S. Pat. No. 5,038,929 to Kubofcik, issued Aug. 13, 1991, is the most relevant prior art that we know of. Kubofcik discloses a sharps disposal system including an array of vertical tubes, resembling the arrangement of test tubes in a rack. Each tube contains a curable liquid and a seal over the top. A used syringe or other sharp instrument is inserted through the seal and into the liquid, which then forms a hardened coating on the instrument.

SUMMARY OF THE INVENTION

In summary, the present invention is hypodermic needle disposal system including a housing forming a vertical and horizontal array of parallel cells, each to receive a tube containing a bonding resin. Each tube includes a rupture seal on its front end. A used needle is directed into a tube to pierce its rupture seal and embed itself in resin. When the resin bonds on the needle, the needle and tube are together removed from the cell for disposal. Tubes are restrained, by gravity locking engagement with the housing, from free movement and from sliding of their cells

DRAWING

FIG. 1 is a view of a typical hypodermic syringe.

FIG. 2 is an exploded view of our needle disposal system.

FIG. 3 is a three-dimensional view of one of the tubes from FIG. 2.

DESCRIPTION

Referring to FIG. 1, a typical hypodermic syringe 10 includes a barrel 11 and a hollow needle 12 removably connected to the barrel by a hub 13. The syringe also includes a plunger, thumb grip, and finger grips, but these do not relate to the invention and are not shown.

A protective needle cap 14 has been removed and the syringe has been used. The cap 14 is not suitable for recapping the used needle because the potential danger of sticking oneself while doing it is too great. Our system, shown in FIGS. 2 and 3, is a safe way to shield and dispose of the needle.

Referring now to FIGS. 2 and 3, the disposal system for the syringe includes a housing 20 with a top 21, bottom 22, left side wall 23, right side wall 24, and back wall 25. Interior members 26 and horizontal members 27 form an array of cells 30 in horizontal rows and vertical columns. The cells are of length "L" from the open front of the housing 20 to the back wall 25, and square in cross section. Strips 28 across the front of the housing 20 from a ridge 29 across the threshold of each cell 30. The housing 20 is adapted for mounting on a wall or other vertical support.

The cells 30 each contain a tube 32 full of a bonding resin 35, such as one of the known resins which are curable on exposure to air, or other adhesive coating material. The tubes 32 are also square in cross section, and are movable in and out of the cells. FIG. 3 shows one of the tubes 32 removed from its cell 30. The tube is longer than the cell 30 by an amount "A", and is therefore of length "L+A" overall. The tube 32 includes on its front end a cover seal or rupture seal 33 which is penetrable by the needle 12.

A transverse groove 34 across the bottom of the tube 32 rests upon the threshold ridge 29 when the tube is in place in its cell 30. This engagement of the groove 34 on the ridge 29 restrains the tube 32 from free movement in the cell to prevent the tube from sliding out of the cell. A slight lift of the front end of the tube 32 will clear it of the ridge 29 and permit removal of the tube from its cell 30.

In an exemplary embodiment:

| | | | | |
|---|---|---|---|---|
| housing 20 is | 21.6 cm high, | 18 cm wide, | 8 cm long (deep); | |
| cells 30 are | 1.7 cm high, | 1.7 cm wide, | 7.7 cm long; | (L = 7.7 cm); and |
| tubes 32 are | 1.5 cm high, | 1.5 cm wide, | 8.6 cm long; | (A = 0.9 cm). |

The disposal system is adapted for use at every point of need, such as patients' rooms, medicine carts, first aid stations, and the like. As soon as a syringe is used it is directed, using only one hand, into a tube 32 (through rupture seal 33) and into the resin 35. Air also enters the tube to initiate bonding of the resin on the embedded needle. When the resin is bonded and relatively solidified on the needle, the syringe 10, needle 12, and tube 32 are removed as a unit from the cell 30 and safely disposed of.

Bonding of the resin is not instantaneous, but it is not necessary for a nurse to hold the syringe and wait for bonding to occur. The needle can simply be left in the tube. The tube 32 remains supported in the housing 20, and it will in turn hold the needle and syringe until bonding has occurred. The solidified syringe/tube unit can be removed together for disposal.

Unlike the prior art where a protective needle cap is replaced on a used needle, this system is a safe one-hand operation. The user does not have to point a used needle at his own fingers and aim it into a slender cap.

The foregoing description of a preferred embodiment of this invention, including any dimensions, angles, or proportions, is intended as illustrative. The concept and scope of the invention are limited only by the following claims and equivalents thereof.

What is claimed is:

1. A hypodermic needle disposal system including:
a housing forming an array of parallel cells extending from front to back within said housing and adapted to receive therein a corresponding number of tubes containing a bonding resin;
each said tube including a rupture seal on the front end thereof;
each said tube nesting within a cell in mating engagement therewith to partially restrain said tube from movement;
said tube adapted to receive a sharp instrument through said rupture seal, to embed said instrument in said resin, and to be removed from its cell for disposal with said instrument.

2. A hypodermic needle disposal system including:
A housing forming a plurality of cells extending from front to back within said housing to receive therein a corresponding plurality of tubes containing a bonding resin;
each said cell including a ridge across the bottom thereof;
a plurality of said tubes nesting within a corresponding plurality of cells of said housing;
each said tube including a rupture seal on the front end thereof;
each said tube including a groove on the bottom thereof to engage a ridge in said cell to thereby restrain free movement of said tube from said cell;
said tube adapted to receive a sharp instrument through said rupture seal, to embed said instrument in said resin, and to be removed from its cell for disposal with said instrument.

3. A hypodermic needle disposal system including:
a housing with top, bottom, side and back walls, and an open front, forming rows of cells length L extending from front to back within said housing to receive therein a corresponding plurality of tubes of length L+A containing a bonding resin;
a plurality of transverse strips across the front of said housing forming a ridge across the bottom of the open end of each said cell;
a plurality of said tubes nesting within a corresponding plurality of cells of said housing;
each said tube including a rupture seal on the front end thereof;
each said tube including a transverse groove across the bottom thereof to engage a ridge on said housing to thereby restrain free movement of said tube from said cell;
said tube adapted to receive a sharp instrument through said rupture seal, to embed said instrument in said resin, and to be removed from its cell for disposal with said instrument.

* * * * *